United States Patent [19]

Morrison

[11] Patent Number: 5,000,742
[45] Date of Patent: Mar. 19, 1991

[54] CAPPING DEVICE FOR SURGICAL NEEDLES

[76] Inventor: Jeff M. Morrison, 3023 Essex Cir., Raleigh, N.C. 27608

[21] Appl. No.: 482,060
[22] Filed: Feb. 20, 1990
[51] Int. Cl.⁵ .............................................. A61M 5/32
[52] U.S. Cl. ..................................... 604/192; 604/263
[58] Field of Search ....................... 604/192, 263, 187

[56] References Cited

U.S. PATENT DOCUMENTS

| | | | |
|---|---|---|---|
| 4,623,336 | 11/1986 | Pedicano et al. | 604/192 |
| 4,799,927 | 1/1989 | Davis et al. | 604/192 |
| 4,892,522 | 1/1990 | Suzuki et al. | 604/192 |

Primary Examiner—John D. Yasko
Attorney, Agent, or Firm—L. Alfred Willson, Jr.

[57] ABSTRACT

The present invention involves a hand-held capping device for surgical needles designed to minimize the risk of accidental needle punctures, characterized by a conical, rimmed shield tapering to a tubular section, a socket being formed at the juncture of the shield with the tubular section in a configuration to receive and grip the hub portion of a conventional surgical needle assembly. The device may include mechanisms to effect needle assembly ejection and/or accommodate assemblies of varying needle length.

5 Claims, 2 Drawing Sheets

CAPPING DEVICE FOR SURGICAL NEEDLES

FIELD OF THE INVENTION

The present invention pertains to medical instruments, more particularly to tools in aid of safe handling, storage and disposal of surgical needles in a manner to minimize accidental needle puncture.

BACKGROUND OF THE INVENTION

As any user of surgical needles will readily attest, their handling has always entailed the risk of inadvertent needle punctures, particularly in the area of the hands. Rare, if ever, would be an instance of where even an occasional, much less frequent, user of surgical needles has not experienced repeated accidental needle punctures.

In cases where the inadvertent puncture is occasioned by a needle of assured sterility, no particular hazard of any significant or seriously threatening consequence is presented. Where, however, a needle is being used to inject or extract fluids into or from a body of unknown and possibly infectious germ state, the risk of needle puncture to the user becomes a matter of grave concern due to fact that such user could become seriously, if not fatally, infected.

Consider the practice of dentistry, where a practitioner would typically come in contact with a number of patients of casual acquaintance on a given day. In many instances, each patient will receive one or more injections of an anesthetic, or the like, depending on the dental procedure on hand. After each injection, good practice demands that the needle be recapped, either for re-use on the same patient, or preparatory to its discard. Heretofore, an inordinate risk of needle puncture has attended each needle recapping procedure, a procedure carried out so often and so routinely as to assure an untold number of instances of inadvertent needle puncture.

The long felt concern over accidental needle punctures by the users of surgical needles for fluid injections and extractions has become magnified due to the increasing prevalence of Acquired Immune Deficiency Syndrome (AIDS). Of course, for many years, there have been other serious diseases known to be transmitted by inadvertent punctures with infected needles, notably hepatitis. Now, with the lurking AIDS virus, practitioners have come to universally feel that even one accidental needle puncture is, emphatically, one too many. There is, accordingly, a keenly felt need for some expedient means towards minimizing the risk of such punctures.

SUMMARY AND OBJECTS OF THE INVENTION

The present invention is embodied in a surgical needle capping device designed to minimize the user's risk of inadvertent needle punctures in the course of handling such needles and more particularly to facilitate the safe capping/recapping of such needles for momentarily laying aside and/or ultimate discard. The device is of simple construction and economical manufacture, and is exemplified in both throw-away and reusable versions, the latter featuring a needle ejecting mechanism.

The subject device is sized for easy hand holding in an operative attitude and essentially comprises a conically-shaped needle entry section tapering to a tubular section and a socket of particular configuration formed within such tubular section at its juncture with such conical section. The socket is configured to receive and grip the hub of a conventional surgical needle and hub assembly against rotational movement to permit threaded engagement/disengagement of the assembly from a conventional surgical syringe. The conical needle entry section is designed to provide an optimum target to intercept and guide a needle point, as it is thrusted toward and into such section, to a safe and secure seating of the needle assembly hub portion within the mating socket while greatly decreasing the risk a chanced needle puncture of the user.

It therefore becomes an object of the invention herein described to provide a capping device for the safe and sure capping/recapping of surgical needles to thereby minimize disease transmission via accidental needle punctures.

Another object of the present invention resides in the provision of a hand-sized surgical needle capping device embodying a simplicity of design of easy and safe use and amenable to economical and precise manufacture in large quantities.

A further object of this invention is a surgical needle capping device of the above referenced character and having provision for the ready ejection of a needle assembly housed therewithin, whereby the capping device may be sterilized for re-use.

Yet another object of the present invention is a surgical needle capping device as above characterized wherein provision is made to accommodate needle assemblies of varying length.

Another object of this invention is to provide a surgical needle capping device as above characterized having an enhanced needle target area and which resists rolling when laid aside.

Other objects and advantages of the present invention will become apparent and will obviously follow a perusal of the following description and the accompanying drawings, which are merely illustrative and not limiting of such invention.

DETAILED DESCRIPTION OF THE INVENTION

Figure 1:
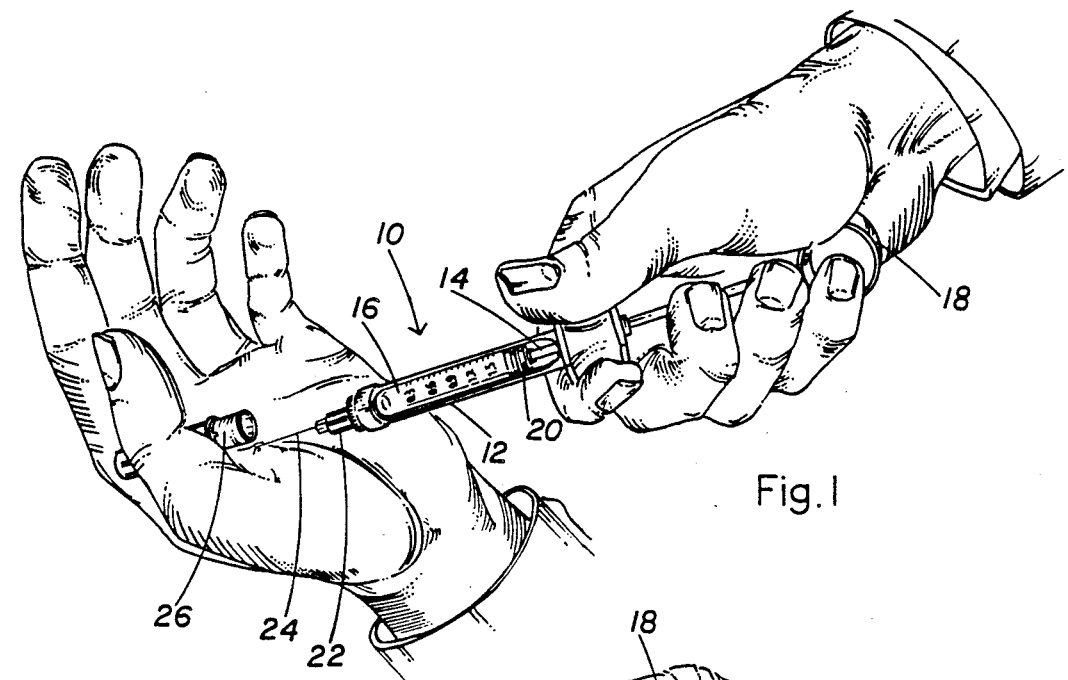
FIG. 1 pictorially illustrates heretofore conventional practice in capping/recapping surgical needles depicting the attendant liability of inadvertent needle punctures.

With further and particular reference to the drawings, FIG. 1 illustrates conventional surgical needle capping procedure and offers a depiction of the all too easily encountered hazard of needle puncture in performing the capping procedure. A conventional syringe 10 for surgical needles would typically comprise a syringe body or barrel 12 having a longitudinal opening 14 to facilitate the insertion of a vial or carpule 16 containing a chosen medication or other fluid. A syringe plunger 18 is mounted at one end of the barrel to be reciprocated longitudinally along such barrel and operative to force a fluid-tight piston element 20 housed within the carpule to urge evacuation of the carpule contents. At the end of the syringe barrel 12 opposite the mounting of the plunger 18, there is provided an externally threaded stud or base, not shown, sized to receive a conventional, internally threaded hub member 22 mounting the needle 24 of a standard surgical needle and hub assembly.

As depicted in FIG. 1, in the course of capping-/recapping a needle for discard or subsequent re-use, a conventional cap 26 (in which the needle and hub assembly typically comes as a sterile package) is held in a fashion therein typified preparatory to the insertion of the needle and hub assembly 22, 24. Once the assembly is secured within the cap 26, it can then be removed from the syringe 10 by a twisting action for replacement with a fresh assembly.

FIG. 2 again illustrates the initiation of a needle capping procedure, but in this case utilizing the capping device 30 according to the present invention. The greatly enhanced protection from accidental needle punctures in utilizing the subject device 30, when compared to the showing in FIG. 1 utilizing conventional capping device 26, becomes readily apparent.

Figure 2:
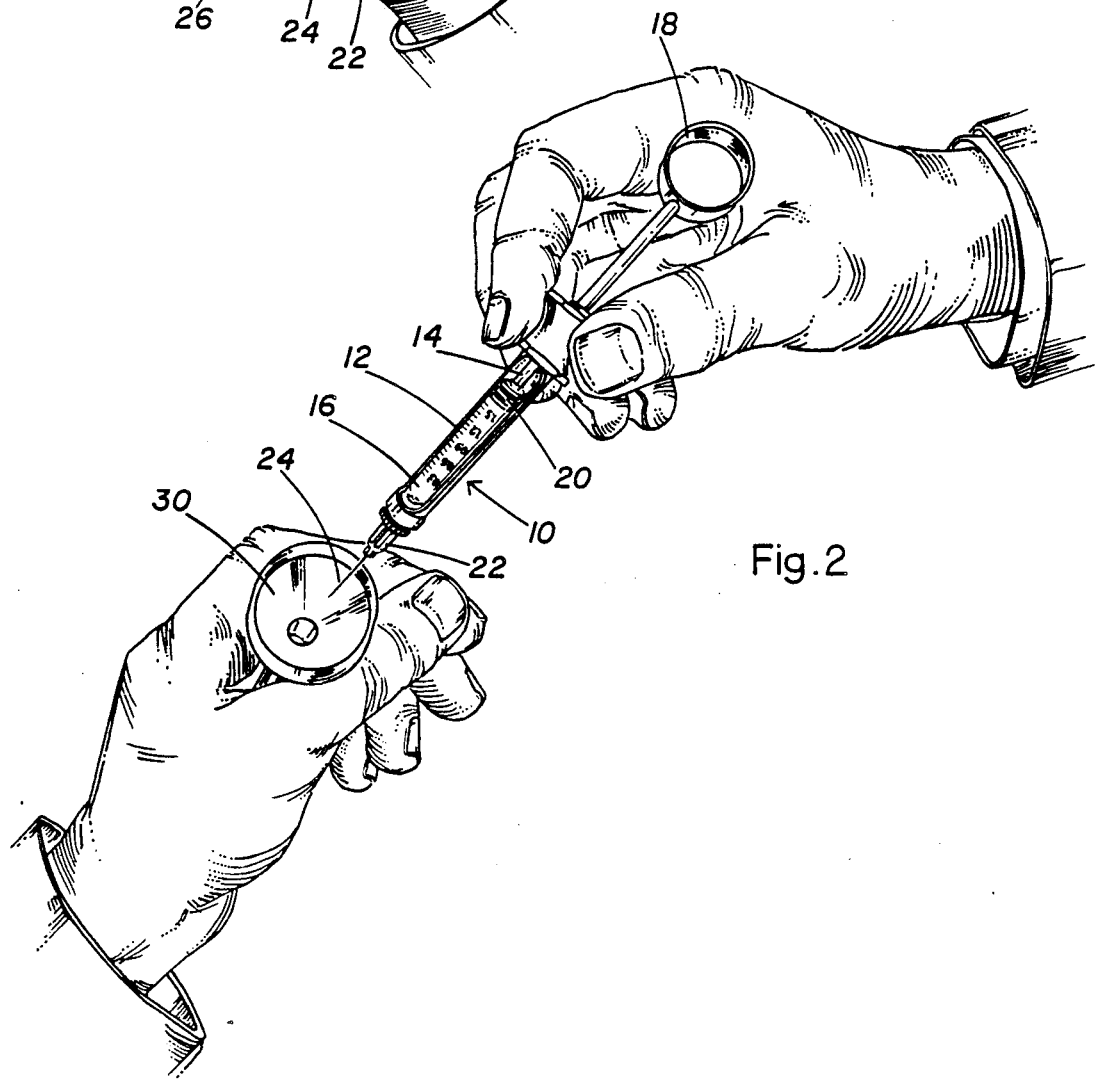
FIG. 2 pictorially illustrates the practice of capping surgical needles utilizing an embodiment of the needle capping device of the present invention.

It should be noted that FIG. 2 depicts a preferred manner of grasping the needle capping device comprising the present invention, namely in fisted fashion. It is recognized, however, that same users may, by virtue of habit or otherwise, prefer to grasp and hold the capping device in some manner different from that shown. In any case, the user will benefit from a greatly reduced chance of accidental needle punctures.

Figure 4:
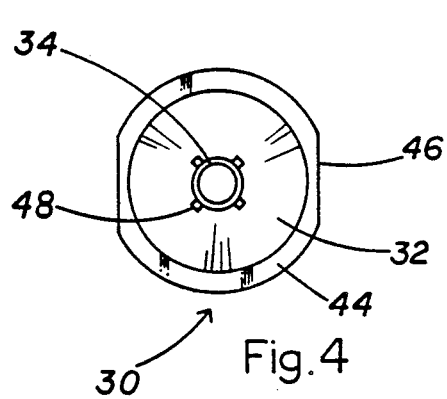
FIG. 4 is an axial perspective view of the needle capping device as viewed from its tubular end.
Figure 5:
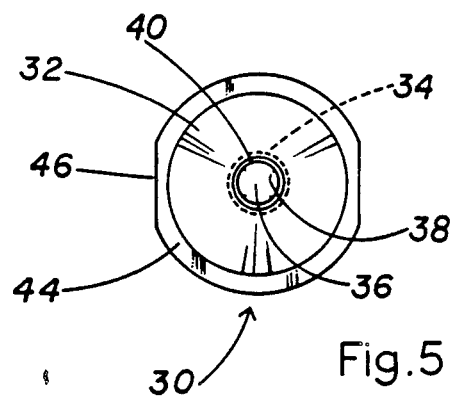
FIG. 5 is a view similar to that of FIG. 4, but from the opposite, conical end of the device.
Figure 3:
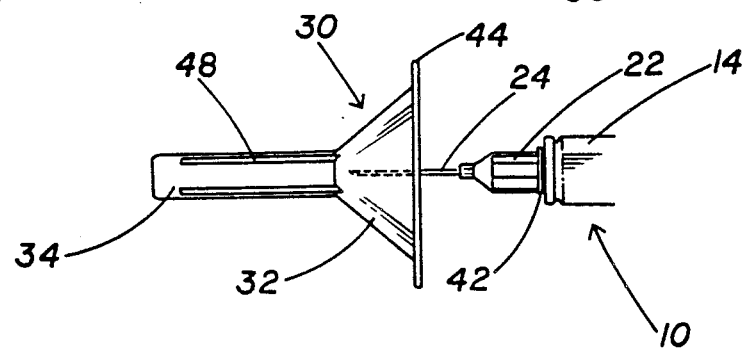
FIG. 3 is a longitudinal perspective view depicting the entry of a conventional surgical needle assembly into an embodiment of the needle capping device of the present invention.

Turning now to the showings in FIGS. 3-5 for a more detailed understanding of the subject needle capping device 30, it is seen that such device is characterized by a conical section 32 tapering to a tubular section 34. The embodiment shown in FIGS. 3-5 is designed for one-time, throw-away usage, wherein the tubular section may be open-ended, but of sufficient length to shield the full length of the needle contemplated for use. The conical and tubular sections are preferably of single piece construction, as by injection molding.

The inner diameter of the tubular section, at least in a zone immediately adjacent its juncture with the conical section, is formed to define a socket 36, as best shown in FIG. 5, having a size and configuration to axially receive and snugly mate with the hub member 22 of a conventional surgical needle and hub assembly. To insure positive rotational gripping between the socket and hub member, longitudinally extending locking ribs 38 may be provided on the inside socket surface to better engage the ribbed surface of a typical needle hub member 22, as depicted in FIGS. 1-3. Preferably, a socket shoulder 40, as best viewed in FIG. 5, is formed at the interface between the tubular and conical sections and bounding the socket entrance to receive and seat hub flange 42 (see FIG. 3) formed at the base of hub member 22, to thereby limit the axial extent of hub member insertion into socket 36.

To optimize the hand fit and feel of the capping device and to provide an enhanced shielded area to the user, a radially outwardly extending rim 44 is integrally formed around the flared end of the conical section. Flattened segments 46 may be formed along the periphery of rim 44 to inhibit the device from rolling about when not in use. Optionally, to further improve gripping of the device and overall stiffness, there may be provided radially spaced ribs 48 extending axially along the outer surface of the tubular section.

Figure 6:
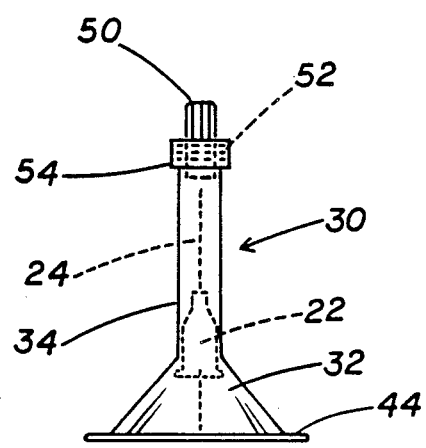
FIG. 6 is a longitudinal perspective view of a needle ejecting version of the capping device depicting a conventional needle and hub assembly seated within such device and the needle ejecting plunger in its biased, needle-receiving position.
Figure 7:
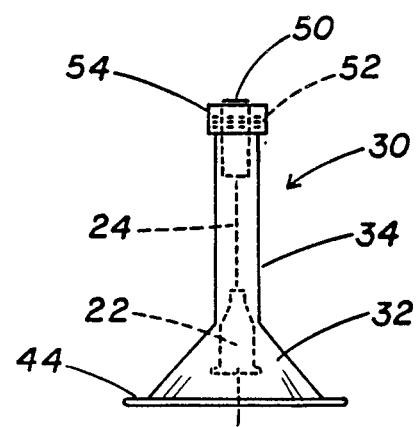
FIG. 7 is a view similar to that of FIG. 6, but depicting the interrelationship between the needle ejecting plunger in its depressed, needle-ejecting position and the disengagement of the hub member of a conventional needle assembly from the capping device.

Turning now to FIGS. 6 and 7, there is depicted a further embodiment of the present invention wherein a needle and hub assembly may readily be ejected from the capping device and discarded, to thereby enable reuse of the device once it has been properly sterilized. Such needle ejection is accomplished by the provision of spring biased plunger 50 mounted to reciprocate axially within the tubular section 34 at the end remote from conical section 32. Any suitable plunger biasing means may be employed, a coil spring 52 being symbolized in FIGS. 6 and 7. A retaining collar 54 is threaded or otherwise affixed on the end of the tubular section to house the plunger biasing element 52 and to retain the plunger 50 within the end of the tubular section 34. FIG. 6 depicts plunger 50 in its biased, needle receiving position, while FIG. 7 depicts the plunger in its depressed, needle ejecting position. It will be noted in comparing FIGS. 6 and 7, that the axial stroke distance of plunger 50 is at least equal to the axial length of hub member 22, as measured from hub flange 42 to the point of reduced hub diameter, i.e. the axial length of the hub member surface contacting the interior wall of socket 36 when the hub member 22 is fully inserted in such socket.

Though not illustrated, it is contemplated that the plunger retaining collar 54 may be modified to provide for axially shifting the biased locus of the plunger 50 to thereby accommodate varying needle lengths.

In striking a balance between comfortable hand-sizing and gripping base, on the one hand, and providing a suitably sized needle target area, it is preferred that the conical section 32 of the present capping device have a flared-end diameter within the range of approximately 30 to 35 mm. and an axial dimension within the range of approximately 15 to 20 mm.; the tubular section 34 have an external diameter of approximately 8 to 10 mm.; the rim 44 have a width of approximately 3 mm.

From the foregoing description and drawings, it will be appreciated that the present invention provides an economical and practical means for significantly enhanced protection from accidental surgical needle punctures at a time of heretofore unequalled concern over infectious disease transmissions by contaminated needles.

The present invention may be practiced in ways not here specifically set forth without departing from the spirit and essential characteristics of such invention. The herein described embodiments of the invention are, therefor, to be considered in all respects as merely illustrative, and not limiting, thereof. All changes and variations coming within the meaning and just range of equivalency of the appended claims are intended to be fully embraced therein.

I claim:

1. A capping device for surgical needles comprising a tubular section; a conical section axially aligned with, tapering towards, abutting and integral with said tubular section; a socket formed axially within said tubular section at the juncture of said tubular and conical sections; said socket having a cross-sectional size and configuration such as to axially receive and releasably engage the hub member of a conventional surgical needle and hub assembly in a manner to resist rotary movement between said capping device and such hub portion; a needle ejecting means comprising: a plunger mounted to reciprocate axially within that end portion of said tubular section remote from said conical section, resilient biasing means urging said plunger in the direction away from said conical section.

2. The capping device of claim 1 and further comprising a plunger stroke limiting means mounting said plunger and operative to define an axial stroke distance of said plunger at least equal to the axial dimension of the area of contact between said socket and a fully inserted hub member.

3. In combination, the capping device of claim 1 and a conventional needle and hub assembly, the hub member of said assembly being seated within and releasably engaged by the socket of said capping device.

4. A capping device for surgical needles comprising a tubular section; a conical section axially aligned with, tapering towards, abutting and integral with said tubular section; a socket formed axially within said tubular section at the juncture of said tubular and conical sections; said socket having a cross-sectional size and configuration such as to axially receive and releasably engage the hub member of a conventional surgical needle and hub assembly in a manner to resist rotary movement between said capping device and such hub portion; a needle and hub assembly ejecting means comprising: a spring-biased plunger mounted to reciprocate axially within said tubular section; plunger retaining means surrounding said plunger and operative to retain said plunger in a first, fully biased position wherein the needle point of a conventional surgical needle and hub assembly of a predetermined length does not impinge upon said plunger when the hub member of such assembly is fully inserted into said socket, and a second, depressed position wherein said plunger transports said assembly axially to a point where said hub member is displaced from said socket, whereby the needle and hub assembly is discharged from said capping device without user contact with such assembly.

5. The capping device of claim 4 wherein said plunger retaining means is further characterized by plunger shifting means engaging said tubular member and operative to shift the axial locus of said plunger retaining means to thereby accommodate varying length needle assemblies.

* * * * *